(12) United States Patent
Olson, Jr. et al.

(10) Patent No.: US 6,730,095 B2
(45) Date of Patent: May 4, 2004

(54) RETROGRADE PLUNGER DELIVERY SYSTEM

(75) Inventors: Stanley W. Olson, Jr., San Ramon, CA (US); Lex P. Jansen, Pleasanton, CA (US); Michael Burns, Boston, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/183,220

(22) Filed: Jun. 26, 2002

(65) Prior Publication Data

US 2004/0002713 A1 Jan. 1, 2004

(51) Int. Cl.[7] .............................................. A61B 17/58
(52) U.S. Cl. ........................ 606/93; 604/218; 604/264
(58) Field of Search ................................ 604/33, 93.01, 604/264, 36, 38, 47, 57, 59, 60, 64, 110, 158, 161, 164.01, 170.01, 170.02, 181, 187, 218, 272, 273, 274; 623/17.11–17.16; 606/92, 93, 94; 600/34, 35

(56) References Cited

U.S. PATENT DOCUMENTS

| | | | |
|---|---|---|---|
| 4,725,264 A | | 2/1988 | Glassman |
| 4,790,819 A | * | 12/1988 | Li et al. ........................ 604/59 |
| 4,808,158 A | | 2/1989 | Kreuzer et al. |
| 4,936,835 A | | 6/1990 | Haaga |
| 5,129,889 A | * | 7/1992 | Hahn et al. .................. 604/265 |
| 5,360,414 A | * | 11/1994 | Yarger ......................... 604/264 |
| 5,741,265 A | * | 4/1998 | Chan ............................ 606/94 |
| 5,843,098 A | * | 12/1998 | Allen et al. .................. 606/144 |
| 6,050,986 A | * | 4/2000 | Hektner ....................... 604/508 |
| 6,214,012 B1 | | 4/2001 | Karpman et al. |
| 6,224,603 B1 | | 5/2001 | Marino |
| 6,241,734 B1 | | 6/2001 | Scribner et al. |
| 6,251,119 B1 | * | 6/2001 | Addis .......................... 606/167 |
| 6,395,007 B1 | | 5/2002 | Bhatnagar et al. |
| 6,402,784 B1 | | 6/2002 | Wardlaw |

FOREIGN PATENT DOCUMENTS

| | | |
|---|---|---|
| EP | 0 406 901 A1 | 1/1991 |
| WO | WO 02/43628 A1 | 6/2002 |

OTHER PUBLICATIONS

U.S. Publication No. 2002/0068974 A1, Kuslich, Stephen D., et al, "Expandable Porous Mesh Bag Device and Methods of Use for Reduction, Filling, Fixation and Supporting of Bone" Publication date Jun. 6, 2002.

U.S. Publication No. 2003/0045885 A1, Margulies, Joseph Y., et al, "Method and Apparatus for Augmentation of the Femoral Neck" Publication date Mar. 6, 2003.

Bhatnagar, et al.; U.S. patent application Publication No. 2002/0049449 A1; entitle "Apparatus and Method for Fixation of Osteoporotic Bobe", Pub. date Apr. 25, 2002.

* cited by examiner

Primary Examiner—David O. Reip
(74) Attorney, Agent, or Firm—Bingham McCutchen LLP

(57) ABSTRACT

Cannulas are provided for delivering therapeutic material to a treatment site. The cannula includes a cannula body with a plurality of openings at the distal end, including a longitudinal opening and a plurality of transverse openings that are axially spaced from each other. The cannula also includes a plunger that is configured to be slidably disposed within the cannula lumen. When the plunger is proximally displaced in the cannula lumen, the plunger seals the distal end and deflects the therapeutic material out the transverse openings. As the plunger is proximally displaced within the lumen, the therapeutic material is forced to perfuse out transverse openings located proximal of the plunger position. In one embodiment, the plunger includes an additional pliable sealable member. In another embodiment, the distal end of the cannula body may be implanted by separating the distal end from the cannula body.

23 Claims, 9 Drawing Sheets

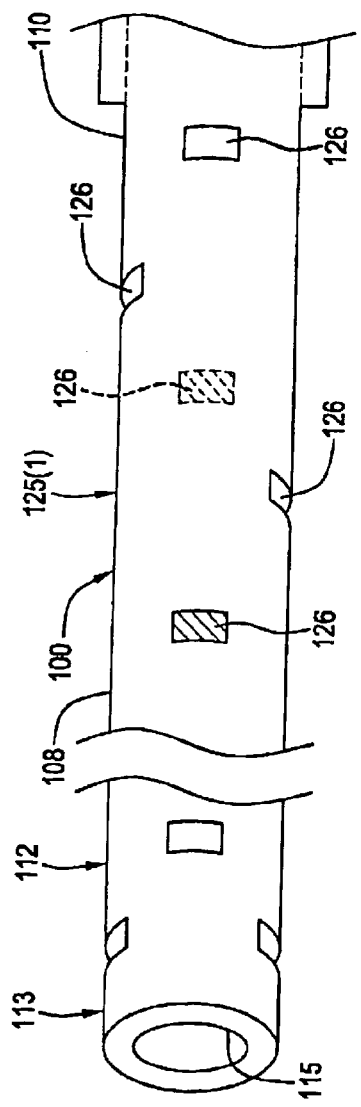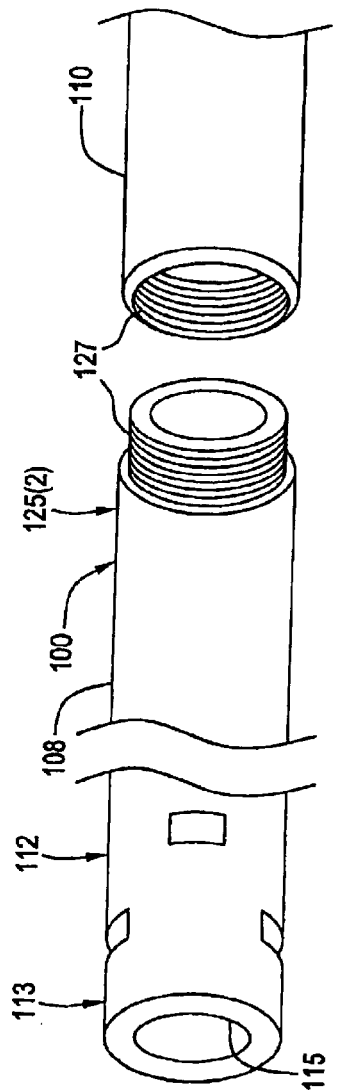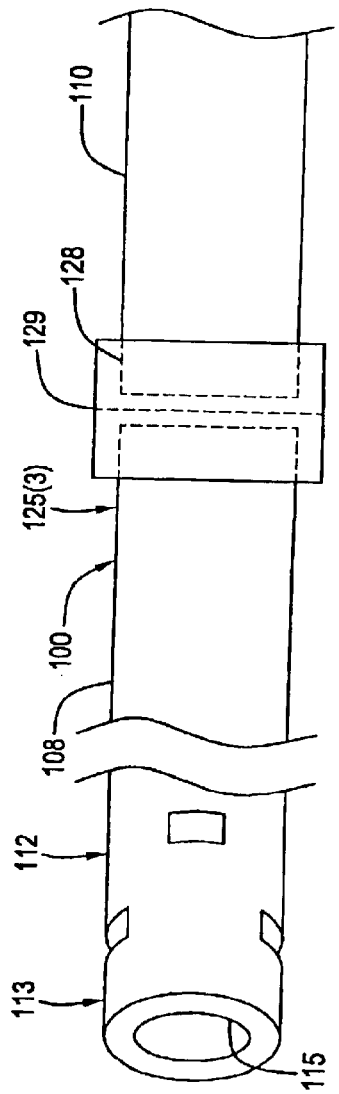

RETROGRADE PLUNGER DELIVERY SYSTEM

FIELD OF THE INVENTION

This invention relates to medical delivery devices, and in particular, to cannula needle or sheath systems for directed delivery of biomaterials.

BACKGROUND

Numerous bone conditions or spinal injury can cause painful collapse of vertebral bodies, including osteopenia (osteoporosis), vertebral hemangiomas, multiple myeloma, necorotic lesions (Kummel's Disease, Avascular Necrosis), metastatic disease and complications from steroid and non-steroidal anti-inflammatory drug (NSAID) use. Osteoporosis is a systemic, progressive and chronic disease that is usually characterized by low bone mineral density, deterioration of bony architecture, and reduced overall bone strength. FIG. 1A depicts the lateral view of typical spinal motion segments 20, with lumbar vertebrae 22, 26, and 28. In contrast, FIG. 1B illustrates a lateral view of a segment of a spinal column that has undergone a vertebral body compression fracture (VCF), as shown by the compressed middle vertebra 26'. VCFs are more common in people who suffer from these medical indications, often resulting in pain, compromises to activities of daily living, and even prolonged disability.

Degenerative and injured spinal disk rehabilitation (pharmacological or gene therapeutic) protocols that delay the progression of intradiscal diseases, or even restore disk health and disk functions, are a part of contemporary research developments and emerging standards of care. The science of spinal intervention has made great strides in recent years. On some occasions, spinal or poly-trauma patients experience VCFs that may be repaired by vertebroplasty and other spinal reconstructive means. Vertebroplasty, which literally means fixing the vertebral body, has been used in the United States since the mid-1990s to treat pain and progressive deterioration associated with VCF. Most often in this vertebroplasty procedure, a bone cement, like opacified polymethylmethacrylate (PMMA), or other suitable biomaterial alternatives or combinations, is injected percutaneously into the bony architecture under radiographic guidance and controls. The hardening (polymerization) of the cement media or the mechanical interlocking of other biomaterials serves to buttress the bony vault of the vertebral body, providing both increased structural integrity and decreased potential for painful micromotion and progressive collapse of the vertebrae and spinal column.

Bone tamps (bone balloons or Kyphoplasty™), a contemporary balloon-assisted vertebroplasty alternative for treatment of VCF, also involves injection of a bone cement into a mechanically created bone void within vertebral body. In this alternative vertebroplasty procedure, a balloon tamp is first inserted into the structurally compromised vertebral body, often through a cannula. The bone balloon is then inflated under high pressure. It is claimed that the expanding balloon disrupts the cancellous bone architecture and physiological matrix circumferentially and directs the attendant bony debris and physiologic matrix toward the inner cortex of the vertebral body vault. The balloon tamp is then deflated and removed, leaving a bony void or cavity. The remaining void or cavity is repaired by filling it with an appropriate biomaterial media, most often bone cement. In most cases, the treatment goals are to reduce or eliminate pain and the risk of progressive fracture of the vertebral body and its likely resulting morbidity, complications, and disability.

Although most of these interventional procedures are an improvement over previous conservative treatments that consisted of bed rest, pharmaceuticals, and/or cumbersome back braces, these methods still suffer from practical difficulties associated with filling the relevant anatomy with the therapeutic material. The precise direction and placement of the therapeutic media is fundamental to optimal patient outcomes. Iatrogenic injury may be reduced or eliminated by the proper application of a delivery technology. In the case of a damaged vertebral body, it is usually imperative that the injected therapeutic materials, e.g., bone cement, sufficiently fill the distal (anterior) end of the vertebral body since this is where the diseased tissue is normally located. When the delivery device enters the vertebral body from the distal end, the distal opening of the delivery device is often quickly encased and clogged with the therapeutic material. And when the delivery device is positioned proximal of the target site, however, the filling of the cavity is often compromised at the distal end.

Accordingly, it would be desirable to provide treatment systems and methods that allow for improved delivery of therapeutic material in the target treatment site.

SUMMARY OF THE INVENTION

The present inventions are directed to a cannula and methods that can be used to deliver therapeutic material to a treatment site in a retrograde manner. Preferably, the inventive cannula is utilized to deliver therapeutic material to bone tissue, such as, e.g., vertebral bodies with compression fractures, but it may also be used at any site in a human or animal that requires the delivery of therapeutic material.

In accordance with a first aspect of the present inventions, the inventive cannula includes a cannula body with a plurality of openings at the distal end that are in fluid communication with a lumen of the cannula body. By way of non-limiting example, the plurality of openings can include a longitudinal opening disposed at the distal tip of the cannula body and one or more transverse openings located proximal to the distal tip. If a plurality of transverse openings are provided, they can be circumferentially offset from each other. The transverse openings can also be arranged into axially spaced groups of transverse openings. The cannula also includes a plunger that is configured to be slidably disposed within a lumen of the cannula body.

Although the present invention should not necessarily be limited by this advantage, the presence of a plurality of openings at the distal end of the cannula body and the plunger provide a means to deliver the therapeutic material to both the proximal and distal ends of the treatment site without having to proximally displace the whole cannula. If there are multiple transverse openings that are circumferentially offset, even perfusion of the therapeutic material is facilitated. In a preferred embodiment, the plunger may include an additional pliable sealable member that provides a tighter seal between the plunger and the inner wall of the cannula body, thereby ensuring or at least minimizing leakage of the therapeutic material between the plunger and the inner wall.

In accordance with a second aspect of the present inventions, a method for delivering implant material into tissue using a cannula is performed. The cannula comprises a cannula body having first and second openings, and a plunger slidably disposed within a lumen of the cannula body. The method comprises inserting the cannula body into a distal section of a tissue, and distally displacing the plunger into a first position distal to the first opening. The implant material is then perfused out of the first opening into the tissue. The plunger is proximally displaced into a second position between the first and second openings, and the implant material is then perfused out of the second opening into the tissue while the plunger is in the second position. By way of non-limiting example, the implant material can be longitudinally perfused out of the first opening, and transversely perfused out of the second opening. This process can be continued if there are any additional openings that are proximal to the second opening. Although the present invention should not necessarily be limited by this advantage, this inventive delivery method provides for a more desirable plume shape of the therapeutic material. Optionally, the distal portion may be separated from the proximal portion of the cannula member, e.g., when the distal tip becomes stuck in the treatment site and it would cause the patient harm if it were to be removed.

In accordance with a third aspect of the invention, the cannula body includes a detachable structure that allows the distal end of the cannula body to be separated from the proximal end. By way of non-limiting example, the detachment structure may include one or more axially spaced notches that allow the cannula body to break into multiple pieces when a shearing force is applied. In a preferred embodiment, the cannula body has a plurality of such notches. Alternatively, the detachment structure may comprise a mechanical junction that would allow the cannula body to separate into multiple pieces when an external force is applied. The mechanical junction may comprise a connective sleeve that detaches into multiple pieces when a shearing or twisting force is applied. In a preferred embodiment, the connective sleeve may contain holes or recessions to aid in the detachment. The mechanical junction may also comprises a threaded junction, wherein the proximal end may be unscrewed from the distal section end. Although the present invention should not necessarily be so limited, the provision of the detachable structure may be desirable when the distal tip becomes stuck in the treatment site and it would cause the patient harm if it were to be removed.

In accordance with a fourth aspect of the invention, a method for delivering implant material into tissue using a cannula is performed. The cannula comprises a cannula body having one or more openings. The method comprises inserting the cannula body into a distal section of a tissue, perfusing the implant material out of the opening into the tissue, and separating the distal end body from the proximal end of the cannula. By way of non-limiting examples, the proximal end is separated from the distal end of the cannula body by detaching the cannula body using a shearing or twisting force or unscrewing the proximal end from the distal end.

Although the present invention should not necessarily be limited by this advantage, this inventive delivery device provides a means for removing the delivery device from the treatment site without further harming the patient if, e.g., the distal tip is intended for implantation or becomes embedded in the treatment site and its removal may pose unnecessary patient risk or threaten patient outcomes if removed.

BRIEF DESCRIPTION OF THE FIGURES

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not, therefore, to be considered limiting of its scope, the invention will be described and explained with additional specificity and detail through the use of the accompanying drawings in which:

FIGS. 5A–5C show side views of delivery assemblies constructed in accordance with a preferred embodiment of the present invention with different detachment technologies;

DETAILED DESCRIPTION OF THE PREFERRED EMBODIMENTS

Referring to FIG. 2, a cannula 100 constructed in accordance with one preferred embodiment is illustrated. The cannula 100 generally includes a cannula body 108 with an associated slidable plunger assembly 105.

Figure 1A:
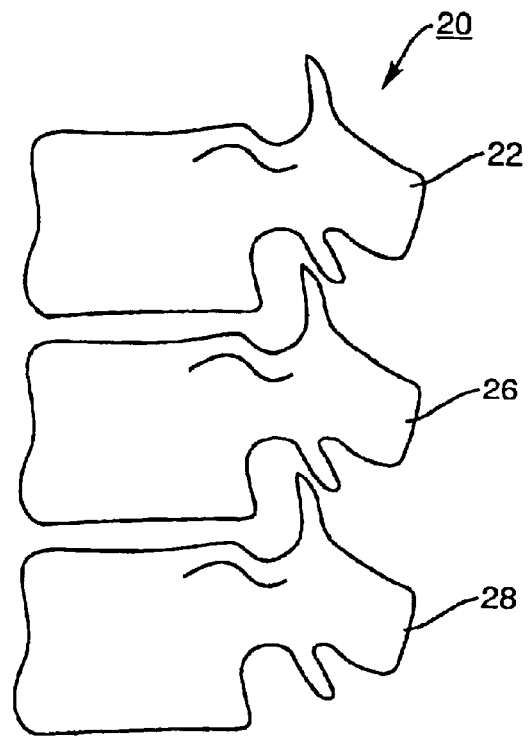
FIG. 1A shows a lateral view of three normal vertebrae.
Figure 1B:
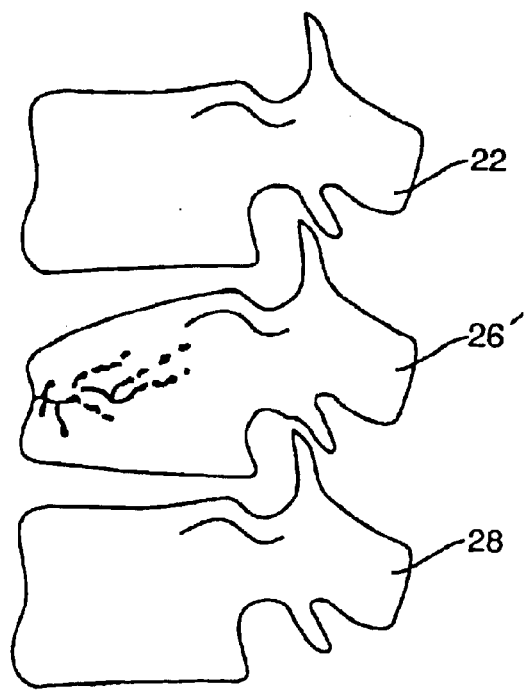
FIG. 1B shows a lateral view of three vertebrae, wherein the vertebral body of the middle vertebra is compressed.
Figure 2A:
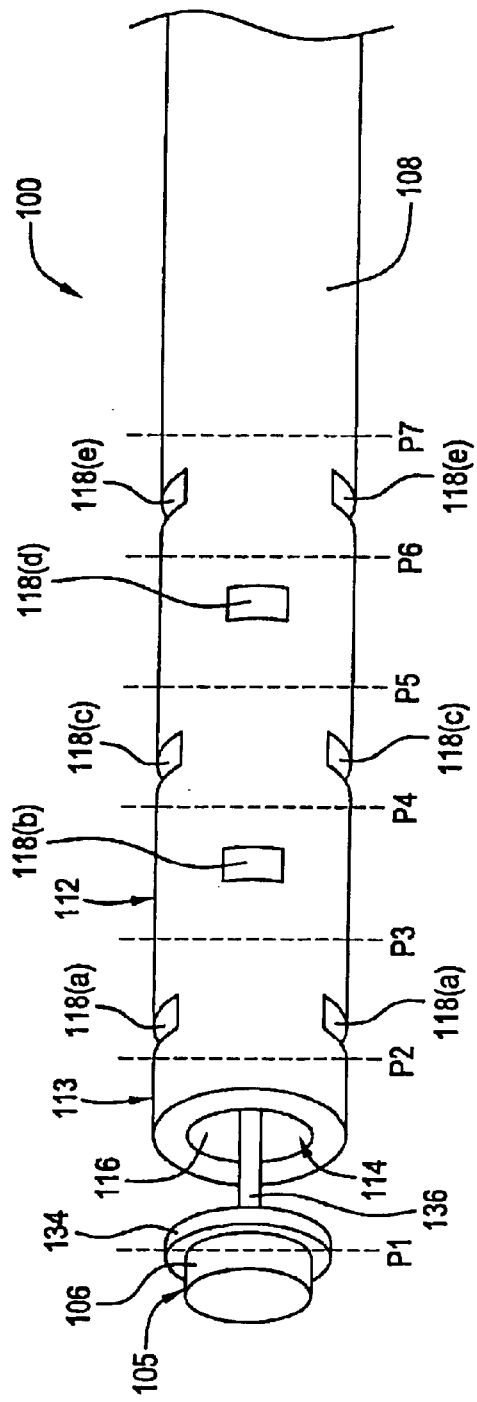
FIG. 2A shows a side view of a delivery assembly constructed in accordance with a preferred embodiment of the present inventions.
Figure 2B:
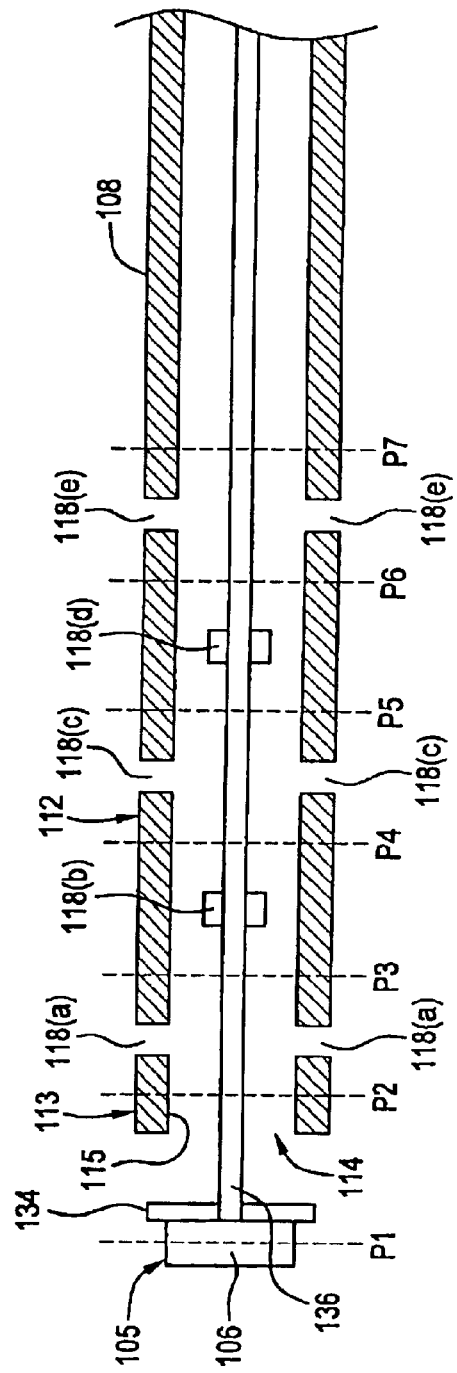
FIG. 2B shows a cross-sectional view of the delivery assembly of FIG. 2A.
Figure 3:
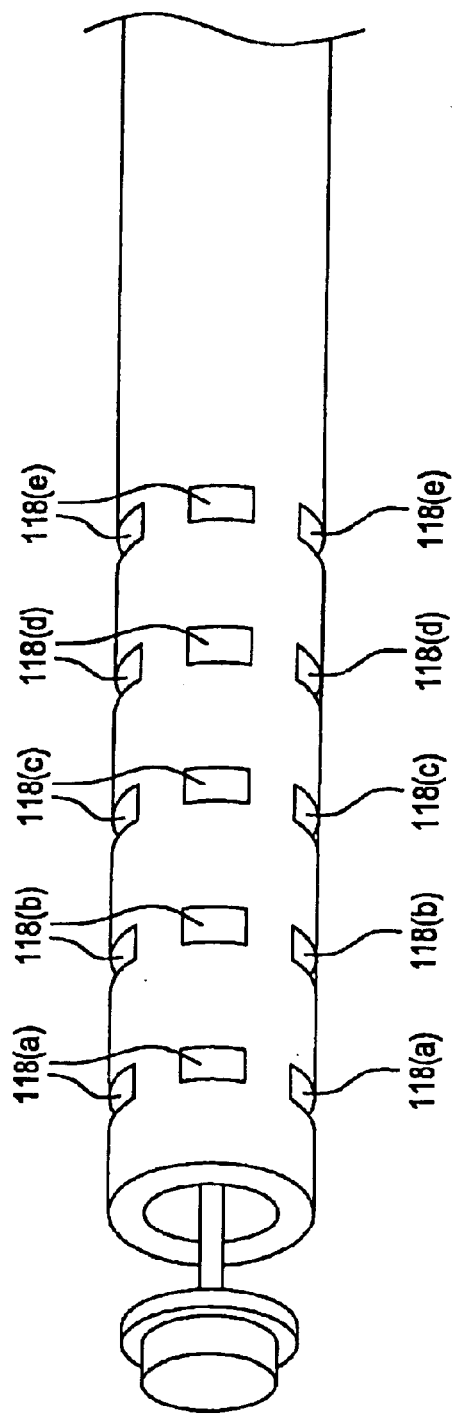
FIG. 3 shows a side view of a delivery assembly constructed in accordance with another preferred embodiment of the present inventions.
Figure 4:
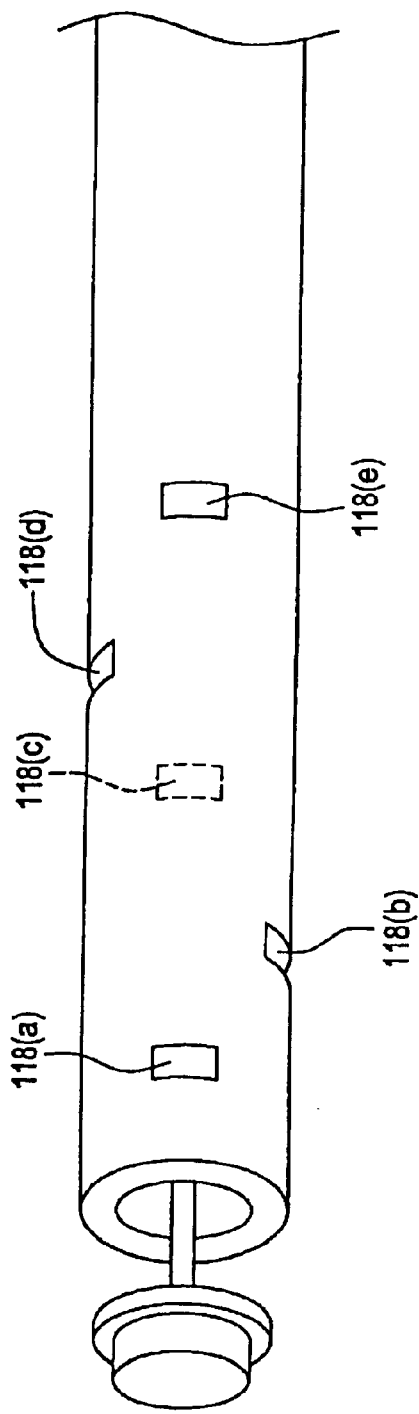
FIG. 4 shows a side view of a delivery assembly constructed in accordance with another preferred embodiment of the present inventions.

The cannula body 108 has a proximal end 110, a distal end 112, and a lumen 114 extending therethrough between the proximal and distal ends 110 and 112. In a preferred embodiment, the distal end 112 of the cannula body 108 is fenestrated. Specifically, the distal end 112 has a plurality of openings including a longitudinal opening 116 at the distal tip 113 of the cannula body 108 and a plurality of axially spaced transverse openings 118 proximal to the distal tip 113. The longitudinal opening 116 and the plurality of transverse openings 118 are in fluid communication with the lumen 114 of the cannula body 108. As illustrated in FIGS. 2A and 2B, the transverse openings 118 are arranged in axially spaced groups of openings 118(a)–(e). Each of the transverse opening groups 118(a)–(e) contains two axially aligned openings 118 that are circumferentially offset from each other by 180°. Each successive transverse opening group is circumferentially offset from adjacent groups by 90°. Alternatively, as illustrated in FIG. 3, each of the transverse opening groups 118(a)–(e) has four axially aligned openings 118 circumferentially offset 90° from each other. Although four openings 118 are herein illustrated, the transverse opening groups 118(a)–(e) may contain any number of openings, such as three axially aligned holes circumferentially offset 60° from each other. Optionally, as illustrated in FIG. 4, the transverse openings are not axially grouped together, but rather each opening 118 is axially and circumferentially offset from each other. For example, successive transverse openings 118(a) and (b) are circumferentially offset from each other by 90°. Although an offset of 90° is herein illustrated, offsets of other angular variations, such as 60°, may also be used.

Preferably, the transverse openings 118 extend proximally up the cannula body 108 for a distance approximately equal to the length of the treatment site. In the case of a vertebral body, the openings 118 may occur periodically for approximately 20 mm up from the distal tip 113. The location of the openings 118 around the circumference of the cannula body 108 in all of these embodiments allow for the therapeutic material to be perfused 360° around the cannula body 108, thereby filling the treatment site in a more even manner. Embodiments in which the openings 118 are not located circumferentially around the cannula body 108 can also be made where it is desired to direct the implant material in a more planar treatment site.

As illustrated in FIGS. 2–4, the transverse openings 118 are rectangular in shape. Transverse openings with different shapes, e.g., circular or elliptical, may also be used. The side walls of the transverse openings 118 may also be curved or otherwise shaped to decrease the likelihood that they will become clogged with therapeutic material during delivery.

The materials used in constructing the cannula body 108 may comprise any of a wide variety of biocompatible materials. In a preferred embodiment, a radiopaque material such as a metal (e.g., stainless steel, titanium alloys, or cobalt alloys) or a polymer (e.g., ultra high molecular weight polyethylene) may be used, as is well known in the art. In another preferred embodiment, where it is desirable to leave a portion of the cannula body 108 implanted in the patient, a bioabsorbable material may be used. These include, but are not limited to, polylactic acid (PLA) and polyglycolic acid (PGA). Alternatively, a biocompatible material, such as polymethylmethacrylate (PMMA) may be used to form the distal tip 113 of the cannula body 108. A combination of materials may also be used. For example, a bioabsorbable material (e.g., PLA) may be used to make the distal end 112 and a metal (e.g., stainless steel) may be used at the proximal end 110.

The plunger assembly 105 includes a plunger 106 and a moveable member 136. The plunger 106 has a proximal end 130 and a distal end 132 and is configured to be slidably received into the lumen 114 of the cannula body 108. As illustrated in FIG. 2, at position P1, the plunger 106 is located distal to the longitudinal opening 116, allowing for longitudinal and transverse openings 116 and 118 to be in fluid communication with the lumen 114 of the cannula body 108. When the plunger 106 is fully received inside the lumen 114 at position P2, located between the longitudinal opening 116 and transverse opening group 118(a), the plunger 106 substantially seals longitudinal opening 116 so that it is no longer in fluid communication with the lumen 114. As a result, a substantial amount of the fluid or viscous material contained within the lumen 114 is deflected from the proximal end 130 of the plunger 106 and is forced to perfuse out of transverse opening groups 118(a)–(e) located proximal to position P2. As the plunger 106 is proximally located at positions P3–P7, transverse opening groups 118(b)–(e), respectively, are sealed off such that they are no longer in fluid communication with lumen 114. For example, when the plunger is at position P4, the plunger 106 substantially seals off longitudinal opening 116 and transverse opening groups 118(a)–(b), forcing the therapeutic material to exit through transverse opening groups 118(c)–(e). The plunger 106 may be made out of the same biocompatible materials used to make the cannula body 108, including any appropriate metal or polymer or any biocompatible material, such as PLA or PGA.

The moveable member 136 is attached to the plunger 106 and is substantially disposed within the lumen 114 of the cannula body 108, allowing for the user to longitudinally displace the plunger 106 within the lumen 114. The moveable member 136 is preferably flexible, allowing it to conform to any curves in the cannula body 108 without breaking. It may be made from the same materials used to make the cannula body 108, such as PLA or PGA. Alternatively, the moveable member 136 may be made from a cable or braided material, such as Titanium. The proximal end of the moveable member 136 may be attached to any appropriate means, e.g. mechanical or electrical, to aid in proximally displacing the plunger 106. Alternatively, the plunger may be manually displaced. The type of material selected for the moveable member 136 will depend on the viscosity of the therapeutic material to be implanted. A highly viscous material, such as some bone cements, may require a moveable member with a high tensile strength, such as braided titanium.

Optionally, the plunger assembly 105 includes an additional pliable sealing member 134 attached to the proximal end 130 of the plunger 106. In its uncompressed state, the diameter of the additional pliable sealing member 134 is slightly larger than the diameter of the lumen 114 of the cannula body 108. Therefore, when the plunger 106 and additional pliable sealing member 134 are slidably received into the lumen 114, the inner wall 115 of the cannula body 108 will compress the additional pliable sealing member 134 a sufficient distance to permit passage of the plunger 106 and additional pliable sealing member 134 within the lumen 114, while sealing the member 134 against the inner wall 115. Therefore, the additional pliable sealing member 134 will provide an improved seal, ensuring that any openings 118 located distal to the plunger 106 position are no longer in fluid communication with the lumen 114. The additional sealing member 134 can be made from an elastopolymer such as "implantable" Ultra-High Molecular Weight Polyethylene (UHMWPE) and silicone, or alternatively, from a shapeable metal, such as nitinol.

Optionally, the cannula 100 may include a detachment structure 125 that enables the distal end 112 to be separated from the proximal end 110 where desired, or alternatively, where the distal end 112 becomes stuck and cannot be retrieved without harming the patient. Where the distal end 112 is separated, the distal end 112 of the cannula 100 is preferably made from an implantable-grade biomaterial, such as a regulatorily-approved stainless steel, polymer, or ceramic. In a preferred embodiment, as illustrated in FIG. 5A, the cannula 100 comprises detachment structure 125(1) that includes a series of axially spaced notches 126 in the wall of the cannula body 108, thereby allowing the cannula body 108 to break into two or more pieces in the presence of a shearing force. Each notch 126 extends radially inwardly from the exterior of the cannula body 108 to just short of the inner wall 115 of the cannula body 108. As with the transverse openings 118 illustrated in FIG. 4, each consecutive notch 126 may be circumferentially offset relative to adjacent notches. For example, successive transverse notches 126 are offset from each other by 90°. Although an offset of 90° is illustrated in this embodiment, circumferential offsets using other angular variations may also be used, such as 60°. Alternatively, the notches 126 can be grouped into axially aligned notches, much like the transverse opening groups 118 shown in FIGS. 2 and 3. For example, for each group, two axially aligned notches 118 can be circumferentially offset by 180° (not shown). It should be noted that the number of notches 126 illustrated is only meant to be an example; a greater or smaller number notches 126 may be provided.

Alternatively, as illustrated in FIG. 5B, the cannula 100 comprises detachment structure 125(2) that includes a mechanical junction. For example, the distal end 112 could be attached to the proximal end 110 of the cannula body 108 with a threaded junction 127. Where implantation of the distal tip 113 is desired, the proximal end 110 could be unscrewed from the distal end 112 using a twisting force.

In another preferred embodiment, as illustrated in FIG. 5C, the cannula 100 comprises detachment structure 125(3) that includes a connective sleeve 128 that couples the proximal and distal ends 110 and 112. The connective sleeve 128 is preferably thin and may be made out of plastic, metal, or other appropriate material. Optionally, the connective sleeve 128 may include holes or recessions 129 to provide a weakened section. Where implantation of the distal tip 113 is desired, an external force, e.g., a shearing or twisting force, could be applied to the connective sleeve 128.

Figure 6:
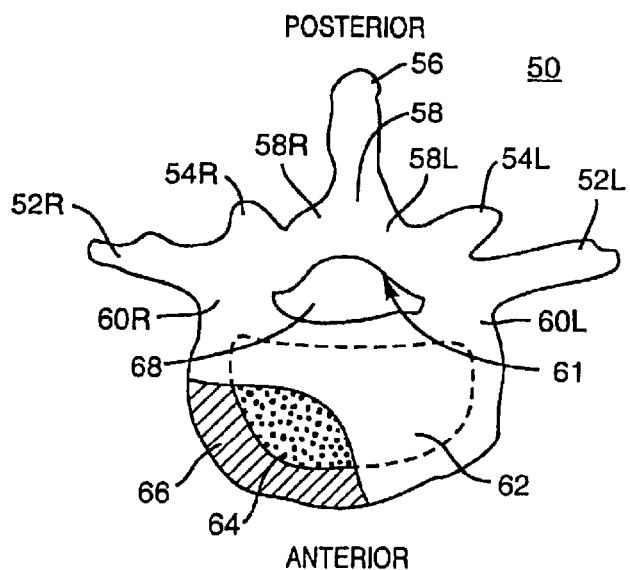
FIG. 6 shows a partially cut-away top view of a lumbar vertebra.

Although, as noted above, use of the cannula 100 of the present invention is not limited to treatment of vertebral ailments, such procedures are discussed here for exemplary purposes. Before discussing such methods of operation, various portions of the vertebra are briefly discussed. FIG. 6 depicts a top view of a vertebra 50. The posterior of the vertebra 50 includes right and left transverse processes 52R, 52L, right and left superior articular processes 54R, 54L, and a spinous process 56. The vertebra 50 further includes a centrally located lamina 58 with right and left lamina 58R, 58L, that lie in between the spinous process 56 and the superior articular processes 54R, 54L, respectively. Right and left pedicles, 60R, 60L, are positioned anterior to the right and left transverse process, 52R, 52L, respectively. A vertebral arch 61 extends between the pedicles 60 and through the lamina 58. The anterior of the vertebra 50 includes a vertebral body 62, which joins the vertebral arch 61 at the pedicles 60. The vertebral body 62 includes an interior volume of reticulated, cancellous bone 64 enclosed by a compact, cortical bone 66 around the exterior. The vertebral arch 61 and body 62 make up the spinal canal, i.e., the vertebral foramen 68; the opening through which the spinal cord and epidural veins pass.

Figure 7A:
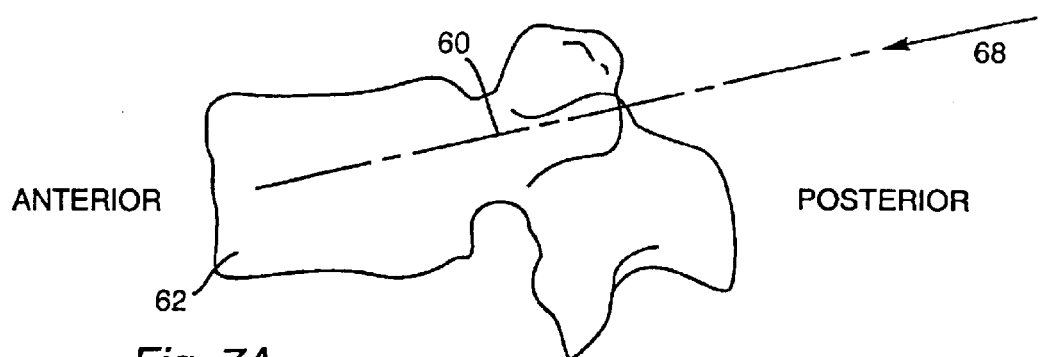
FIG. 7A shows a lateral view of one posterior access route to the anterior vertebral body shown in FIG. 6.
Figure 7B:
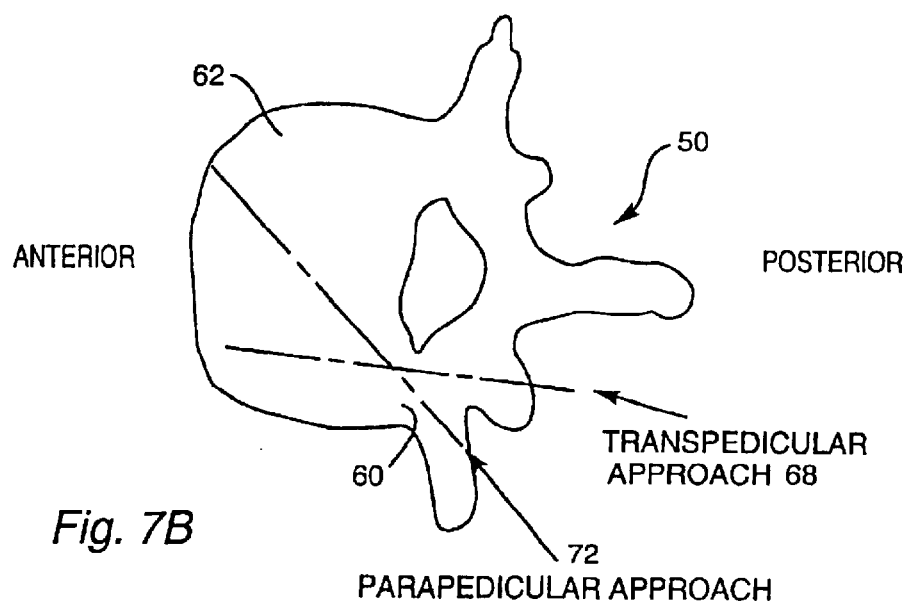
FIG. 7B shows a top view of transpedicular and parapedicular routes to the anterior vertebral body shown in FIG. 6.

The physician can choose from a variety of approaches to insert the cannula 100 into the vertebral body 62. As depicted in FIG. 7A, in the transpedicular approach, access to the cancellous bone in the vertebral body 62 is gained through the pedicle 60. Alternatively, as depicted in FIG. 7B, a parapedicular approach 72 may be used in which access is gained through the side of the vertebral body 62 beside the pedicle 60. This approach may be selected if the compression fracture has resulted in collapse of the vertebral body 62 below the plane of the pedicle 60. Still other physicians may opt for an intercostal approach through the ribs (not shown) or a more clinically challenging anterior approach (not shown) to the vertebral body 62.

Figure 8A:
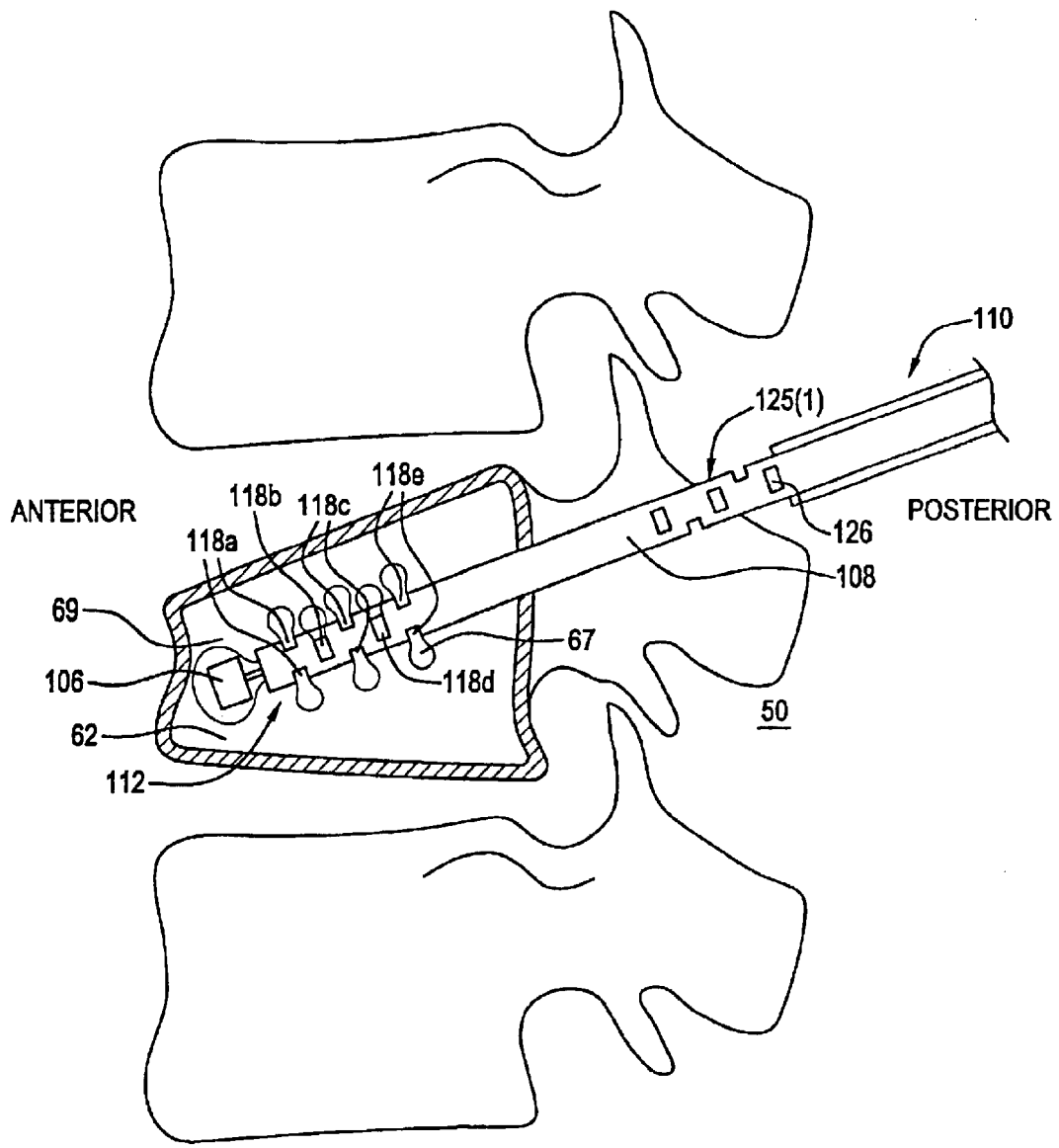
FIGS. 8A–8C shows a side elevational view of the cannula of FIG. 2 inserted into a vertebral body.

Referring now to FIGS. 8A–8D, an exemplary procedure for treating a fractured vertebra 50 using the cannula 100 will be discussed. Turning specifically to FIG. 8A, a transpedicular approach is used to gain access to the interior of the vertebral body 62 through a naturally occurring bore or passage 67 in the vertebra 50 formed as a result of the condition to be treated. Alternatively, a bore or passage 67 in the bone may be formed with a drill. The size of the bore or passage 67 into the interior of the vertebral body 62 should be slightly larger than the external diameter of the cannula body 108 so that it can be inserted through the bore or passage 67 into the vertebral body 62. In addition, the physician may further create a cavity 69 within the vertebral body 62 before insertion of the cannula body 108 if desired. This may be accomplished using any surgical tool to carve out a cavity or perhaps by using an additional expandable or deployable device, such as those used in angioplasty or atraumatic tissue expansion or dissection.

The distal end 112 of the cannula body 108 is preferably placed in the center of the anterior vertebral body void or vault 62, with the plunger 106 positioned distal of the longitudinal opening 116. Once the cannula body 108 is properly placed and the fluid or viscous material has been introduced into the lumen 114, the physician may then apply some form of pressure, e.g., a syringe or power device, to force the material out the longitudinal and transverse openings 116 and 118 at the distal end 112. As illustrated in FIG. 8A, when the plunger 106 is at position P1 (shown in FIG. 2), the majority of the fluid or viscous material will perfuse out the longitudinal opening 116, although some will also perfuse out the transverse openings 118.

Figure 8B:
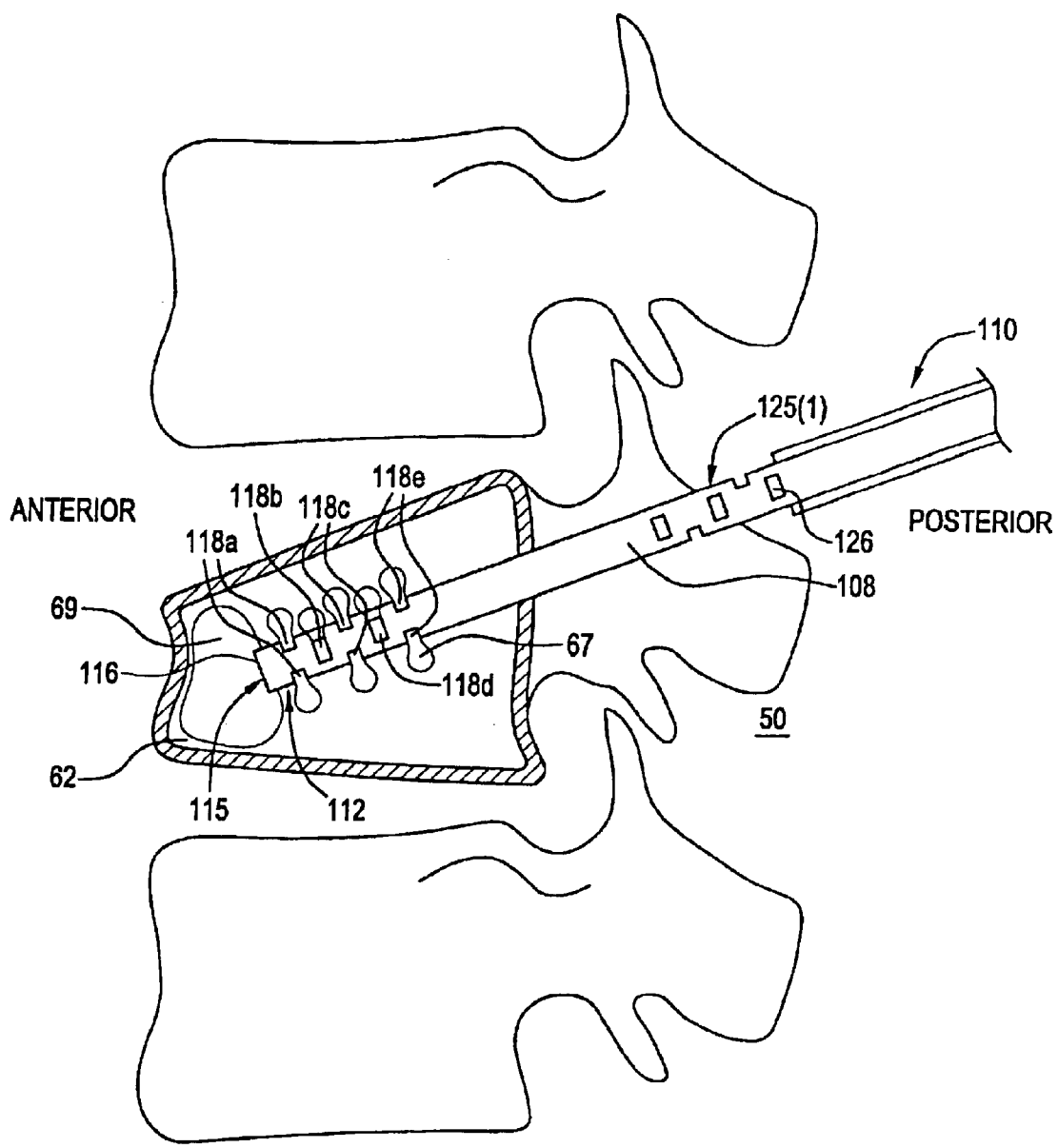
Figure 8C:
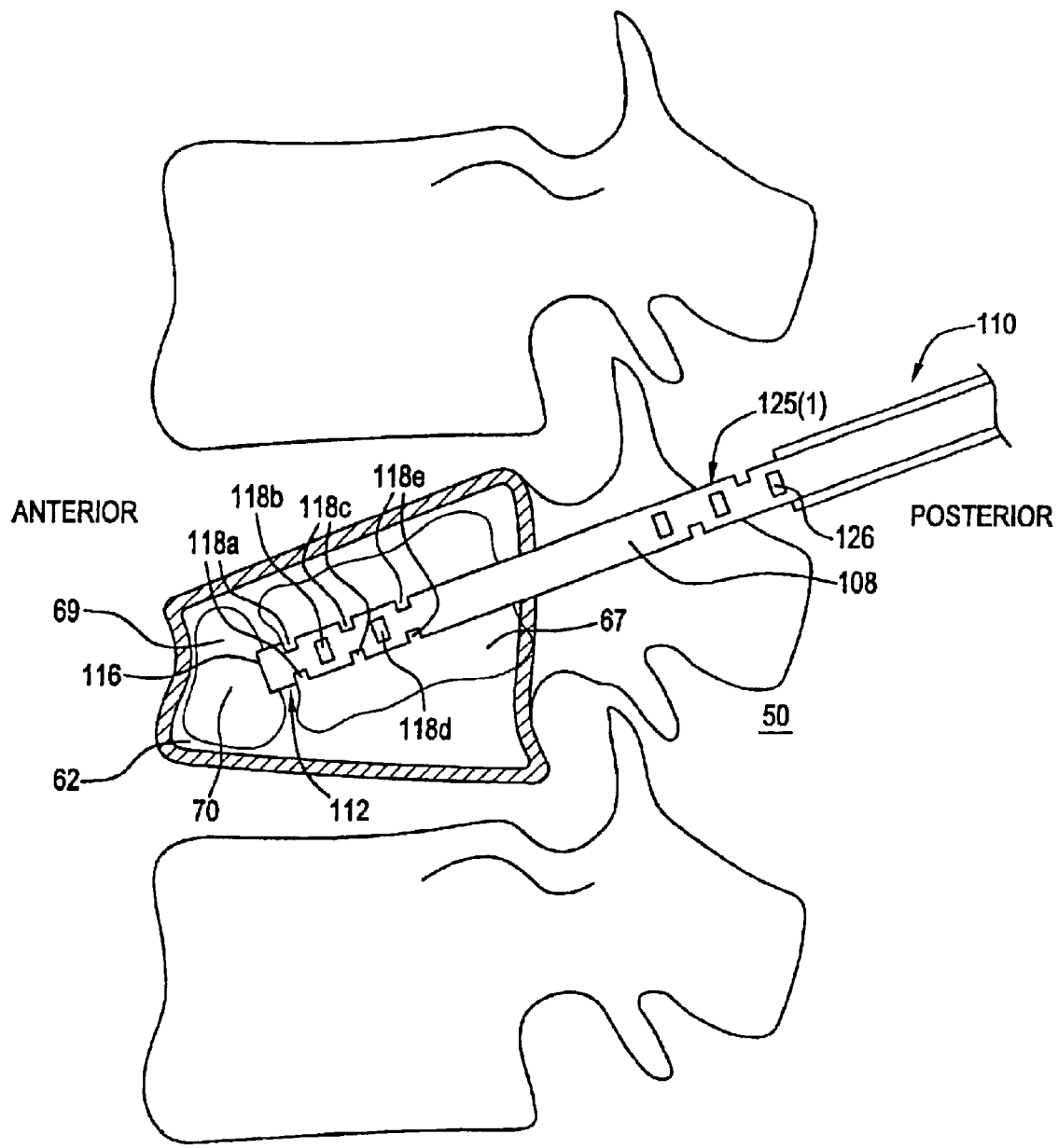
Figure 8D:
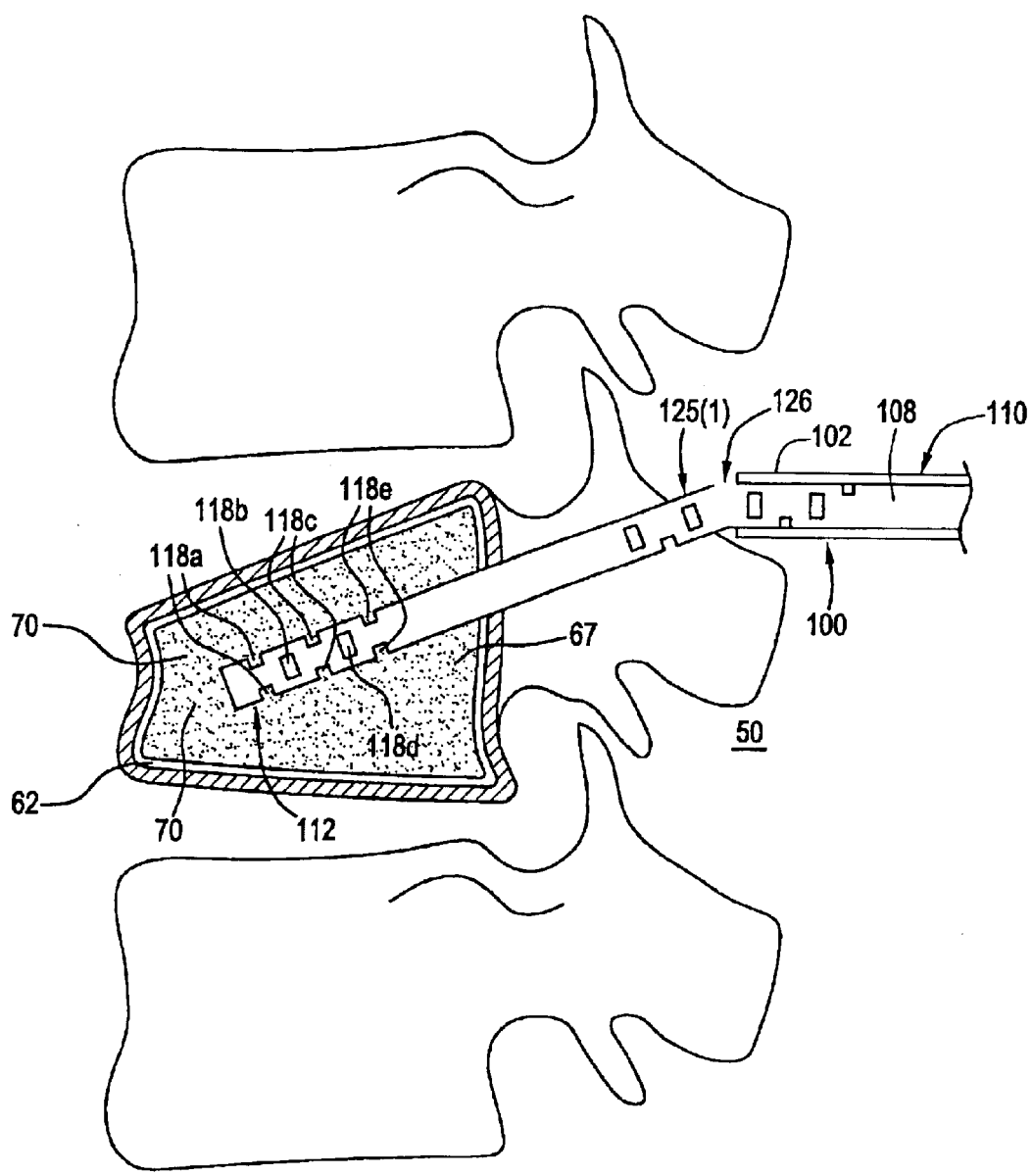
FIG. 8D shows a side elevational view of a severed cannula of FIG. 8A.

Referring now to FIG. 8B, the physician can then proximally displace the plunger 106 by retracting the attached moveable member 136, either by manual, mechanical, or electrical means. As the plunger 106 is proximally displaced into the lumen 114 to a position P2 (shown in FIG. 2) between the longitudinal opening 116 and the distal-most transverse opening group 118(*a*), the plunger 106 substantially seals off the longitudinal opening 116, thereby forcing the fluid or viscous material to perfuse through the transverse opening groups 118(*a*)–(*e*). As the distal portion of the treatment site is filled, the plunger 106 can again be proximally displaced to a new position P3 (shown in FIG. 2) between transverse opening groups 118(*a*) and (*b*), thereby substantially sealing off the longitudinal opening 116 and transverse opening group 118(*a*). This forces the implant material to perfuse out transverse openings located proximal of transverse opening group 118(*a*), i.e., transverse opening groups 118(*b*)–(*e*). As illustrated in FIGS. 8C–8D, the process of proximally displacing the plunger 106 to positions P4–P7 can be repeated until the therapeutic site is filled as desired. By sequentially forcing the implant material out of the transverse openings 118, a more even distribution of the implant material in the treatment site results without having to proximally displace the entire cannula body 108. Where a bone cement is delivered to a vertebral body 62, this delivery technique results in a more desirable cloud-like plume shape 70 of the bone cement, which provides increased structural integrity for the damaged vertebra. Although the implant material has been described as being delivered within the vertebra 50 using the cannula 100 illustrated in FIG. 2A, other cannulae, such as those illustrated in FIGS. 3 and 4 can be used as well.

Where implantation of the distal end 112 of the cannula body 108 is desired, or where it cannot be removed without harming the patient, the distal end 112 can be separated or severed from the proximal end 110 and left in the vertebra 50. As illustrated in FIG. 8D, the physician, with the aid of well known visualization and imaging techniques, may slip outer tube 102 over the exposed proximal end 110 of the cannula body 108 until the free end of the outer tube 102 is aligned with the first notch 126 external to the vertebra. The cannula body 108 can then be severed by applying a shearing force, urging the proximal end 110 laterally in the direction that tends to separate the selected notch 128. Alternatively, the distal end 112 may be severed by applying an external twisting force, depending on the design of the cannula body 108. The proximal end 110 of the cannula body 108 can then by extracted from the patient. Any of the other detachment structures 125 can be used as well to separate the distal and proximal ends 112 and 110.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed:

1. A cannula for use in delivering therapeutic material, comprising:
    a cannula body having a proximal end, a distal end, and a lumen extending between the proximal and distal ends; and
    a plunger configured to be slidably disposed within the lumen;
    wherein the distal end of the cannula body has one or more openings in fluid communication with the lumen, and a distal opening for allowing the plunger to exit distally from the lumen.
2. The cannula of claim 1, further comprising a detachment structure that allows the distal end to be separated from the proximal end of the cannula body.
3. The cannula of claim 2, wherein the detachment structure comprises one or more axially spaced notches that allows the cannula body to break into two or more pieces in the presence of a shearing or twisting force.
4. The cannula of claim 3, wherein the one or more notches comprises a plurality of notches.
5. The cannula of claim 3, wherein the detachment structure comprises a plurality of the notches circumferentially offset from each other.
6. The cannula of claim 2, wherein the detachment structure comprises a mechanical junction that allows the cannula body to separate into two pieces in the presence of an external force.
7. The cannula of claim 6, wherein the mechanical junction comprises a connective sleeve that allows the cannula body to separate into two pieces in the presence of the external force.
8. The cannula of claim 6, wherein the mechanical junction comprises a threaded junction that allows the cannula body to separate into two pieces in the presence of a rotational force.
9. The cannula of claim 1, wherein the plunger further comprises a pliable sealing member.
10. The cannula of claim 1, wherein the cannula body comprises a biocompatible material.
11. The cannula of claim 1, wherein the plunger comprises a biocompatible material.
12. The cannula of claim 1, wherein each of the one or more openings comprises a transverse opening proximal to the distal tip of the cannula body.
13. The cannula of claim 1, wherein the distal end of the cannula body includes a plurality of the openings, each of the plurality of the openings comprises a transverse opening proximal to the distal tip of the cannula body.
14. The cannula of claim 13, wherein the transverse openings are circumferentially offset from each other.
15. The cannula of claim 13, wherein the transverse openings is arranged into axially spaced groups.
16. The cannula of claim 15, wherein each transverse opening group comprises a plurality of axially aligned openings.
17. A cannula for use in delivering therapeutic material, comprising:
    a cannula body having a proximal portion, a distal portion, and a plurality of axially spaced notches that allow the distal portion of the cannula body to be separated from the proximal portion of the cannula body in the presence of a shearing or twisting force,
    wherein the distal portion of the cannula body has a dimension that allows the distal portion to be completely enclosed within a body cavity after the distal portion is separated from the proximal portion.
18. A cannula for use in delivering therapeutic material, comprising:
    a cannula body having a proximal portion, a distal portion, and a plurality of notches circumferentially offset from each other that allow the distal portion of the cannula body to be separated from the proximal portion of the cannula body in the presence of a shearing or twisting force,
    wherein the distal portion of the cannula body has a dimension that allows the distal portion to be completely enclosed within a body cavity after the distal portion is separated from the proximal portion.
19. A cannula for use in delivering therapeutic material, comprising:
    a cannula body having a proximal portion, a distal portion, and a detachment structure, the detachment structure allowing the distal portion of the cannula body to be separated from the proximal portion of the cannula body;
    wherein the distal portion of the cannula body has a dimension that allows the distal portion to be completely enclosed within a body cavity after the distal portion is separated from the proximal portion of the cannula body, and wherein the cannula body comprises a bioabsorable material.
20. The cannula for use in delivering therapeutic material, comprising:
    a cannula body having a proximal portion, a distal portion, a lumen extending through the body, and a detachment structure, the detachment structure allowing the distal portion of the cannula body to be separated from the proximal portion of the cannula body;
    wherein the distal portion of the cannula body has a dimension that allows the distal portion to be completely enclosed within a body cavity after the distal portion is separated from the proximal portion of the cannula body, the cannula body comprising a plurality of the openings in fluid communication with the lumen, each of the plurality of openings comprising a transverse opening proximal to the distal tip of the cannula body.
21. The cannula of claim 20, wherein the transverse openings are circumferentially offset from each other.
22. The cannula of claim 20, wherein the transverse openings is arranged into axially spaced groups.
23. The cannula of claim 20, wherein each transverse opening group comprises a plurality of axially aligned openings.

* * * * *